(12) United States Patent
Mottier

(10) Patent No.: US 7,996,159 B2
(45) Date of Patent: Aug. 9, 2011

(54) GAS DETECTOR SYSTEM AND METHOD

(75) Inventor: Francois Mottier, Stamford, CT (US)

(73) Assignee: Delphian Corporation, Northvale, NJ (US)

(*) Notice: Subject to any disclaimer, the term of this patent is extended or adjusted under 35 U.S.C. 154(b) by 385 days.

(21) Appl. No.: 12/207,834

(22) Filed: Sep. 10, 2008

(65) Prior Publication Data

US 2010/0063748 A1  Mar. 11, 2010

(51) Int. Cl.
*G01N 30/74* (2006.01)
(52) U.S. Cl. ............... 702/24; 356/437; 356/432
(58) Field of Classification Search ............... 702/24
See application file for complete search history.

(56) References Cited

U.S. PATENT DOCUMENTS

| | | | | |
|---|---|---|---|---|
| 5,542,285 | A * | 8/1996 | Merilainen et al. | 73/23.21 |
| 5,572,031 | A * | 11/1996 | Cooper et al. | 250/343 |
| 5,886,348 | A * | 3/1999 | Lessure et al. | 250/339.13 |
| 6,026,673 | A * | 2/2000 | Santini | 73/1.06 |
| 6,138,674 | A * | 10/2000 | Gull et al. | 128/204.21 |
| 6,545,278 | B1 * | 4/2003 | Mottier et al. | 250/339.13 |
| 7,150,353 | B2 * | 12/2006 | Lord | 206/0.6 |
| 7,288,766 | B2 * | 10/2007 | Uchida et al. | 250/338.5 |
| 2009/0188297 | A1 * | 7/2009 | Willett et al. | 73/1.06 |

OTHER PUBLICATIONS

"Gas Explosion Handbook", Chapter 4, Combustion Properties of Fuel-Gas Mixtures, p. 2, Fig. 4.2. http://www.gexcon.com/handbook/gexhbchap4.htm, 2007.*
(("Equation of State (Ideal Gas)". Glenn Research Center, NASA,, http://www.grc.nasa.gov/WWW/K-12/airplane/eqstat.html)), 2000.*
Ultima Xir Gas Monitor, Mine Safety Appliances Company, PO Box 426, Pittsburgh, PA 15230, http://www.msanorthamerica.com/catalog/product1562.html.*
Michael G. Zabetakis, "Flammability Characteristics of Combustible Gases and Vapors", Washington, U.S. Dept. of the Interior, Bureau of Mines, 1965.*

* cited by examiner

*Primary Examiner* — Eliseo Ramos Feliciano
*Assistant Examiner* — Alexander Satanovsky
(74) *Attorney, Agent, or Firm* — Fitch, Even, Tabin & Flannery

(57) ABSTRACT

A method, system, and apparatus for sensing gases includes a gas detector with at least one light emitter and at least one light detector configured to detect an intensity of light at wavelengths of light indicative of target gas(es). The system also includes a processor circuit and a data storage device in communication with the gas detector and configured to determine an amount of target gas in the volume of the gas-air mixture and to determine a lower explosive limit ("LEL") level for at least one target gas in the gas-air mixture. The processor is configured to receive data regarding temperature and relative humidity of the gas-air mixture such that the processor circuit can adjust the LEL according to the temperature and humidity. Temperature and humidity sensors may be included to sense these conditions for inputting to the processor.

29 Claims, 2 Drawing Sheets

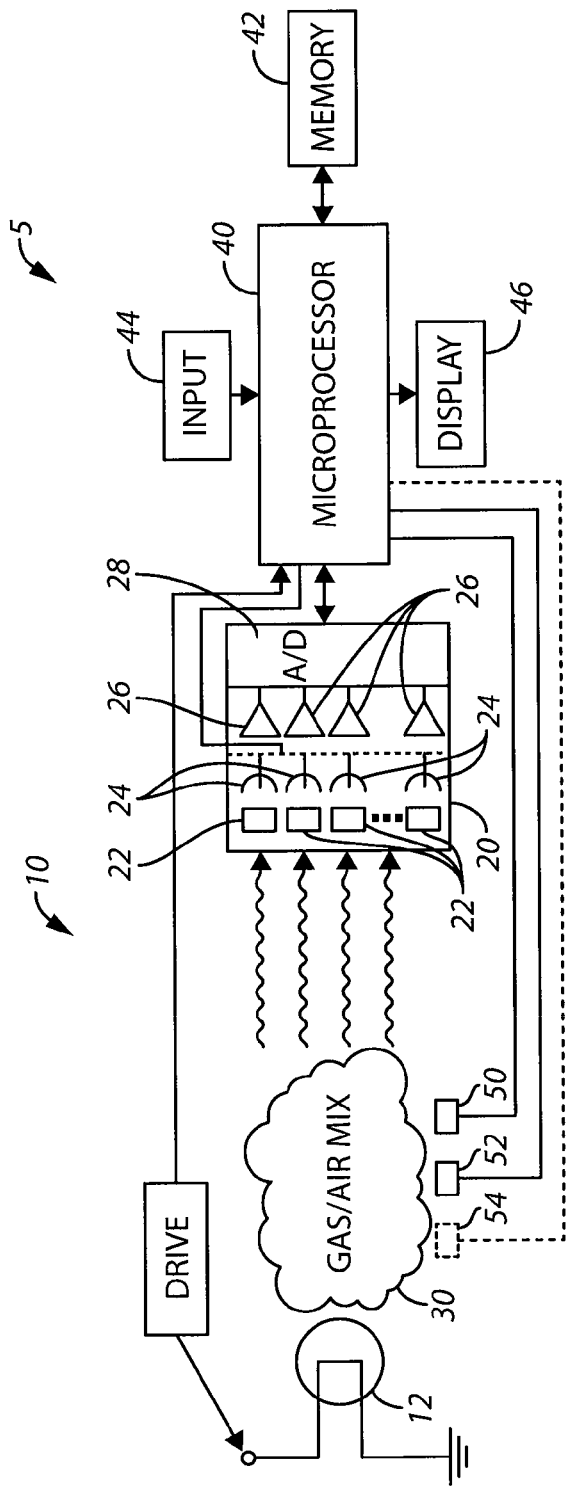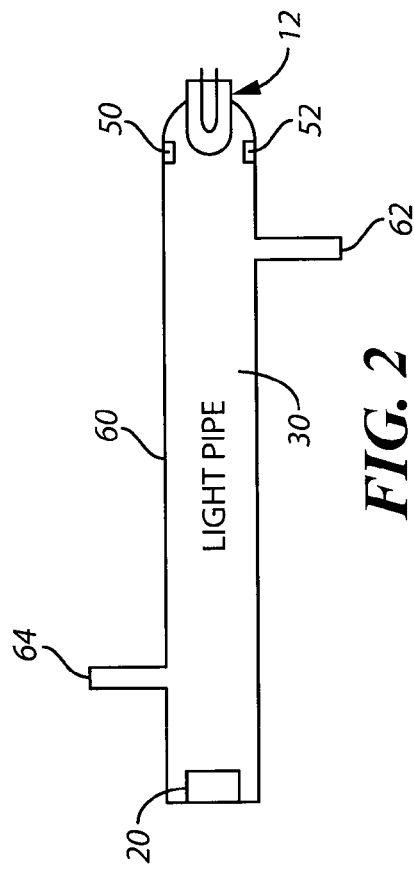

GAS DETECTOR SYSTEM AND METHOD

TECHNICAL FIELD

This invention relates generally to gas detection systems and more particularly to the accurate determination of explosive levels of gases in a given environment.

BACKGROUND

The detection of various gases is necessary to determine whether it is safe to work in certain conditions. In various industrial work areas, certain explosive gases may be released into the atmosphere that can create a dangerous situation, including for example, various hydrocarbon gases such as cyclohexane, butane, bivinyl, and methane among other gases. Such gases generally will become explosive, and thus dangerous, when the amount of the gas reaches a certain level relative to the amount of oxygen in the air. This ratio between the target gas and oxygen is often expressed as a lower explosive limit level ("LEL level") of the gas, often denoted "% LEL" as a percentage of the target gas in the atmosphere because the amount of oxygen in air is generally constant. Accordingly, under certain work situations where explosive gases may be present, it is imperative to test for the amount of such gases in the air to avoid a dangerous condition.

Various devices are known to detect such dangerous gases. Certain of the known devices detect such gases by passing light through a volume of gas-air mixture and detecting the attenuation of certain wavelengths of the light. Because different gases absorb different wavelengths of light, one can configure such a device to determine the total amount of such gases in the tested volume based on the amount of absorption of light at the specific wavelengths. Such devices then take the measured amount of the target gas and determine the LEL level based on the known conditions of the standard atmosphere.

U.S. Pat. No. 6,545,278 issued to Mottier et al. describes a device that analyzes a gas-air mixture for dangerous gases via infra-red analysis, corrects for variations in sensor operation due to temperature through saved correction tables, and corrects for pressure variations due to altitude based on saved correction tables. Although such a device as described works well under most conditions, the device, however, does not correct for the effect of certain atmospheric conditions on the measured gas-air mixture and potentially is not precise at certain relatively extreme operation conditions.

For example, in situations of high humidity, the amount of oxygen in the air is lessened because of displacement by the large concentration of water vapor in the air. Similarly, large variations in temperature or pressure can increase the error of some devices, especially in high humidity conditions, because some devices do not include error correction based on changes to the gas-air mixture caused by such atmospheric variations. For example, the device described in U.S. Pat. No. 6,545,278, corrects for temperature induced variations in the operation of the light detectors, but not for measurement changes caused by a change in the gas-air mixture as a result of temperature or humidity variations. Although such measurement variations caused by normal atmospheric variations does not introduce significant error, increased error in such devices due to relatively extreme humidity, temperature, and pressure in certain non-typical atmospheric conditions may result in workers being present in dangerous conditions or may result in unnecessary work stoppages based on false warnings of dangerous conditions.

SUMMARY

Generally speaking, pursuant to these various embodiments, a method, system, and apparatus for sensing gases includes a gas detector with at least one light emitter and at least one light detector configured to detect the fraction of light absorbed by a target gas at wavelengths of light indicative of the target gases. These wavelengths correspond to a target gas absorption spectrum in a volume of gas-air mixture. The system also includes a processor circuit and a data storage device in communication with the gas detector. Based upon data collected by the gas detector, the processor circuit and data storage device are configured to store data and determine an amount of target gas in the volume of the gas-air mixture and to determine a lower explosive limit ("LEL") level for at least one target gas in the gas-air mixture. The processor is configured to receive data representative of temperature and relative humidity of the gas-air mixture such that the processor circuit can calculate and determine the LEL taking into account the temperature and relative humidity, and optionally pressure. A temperature sensor and a humidity sensor can be disposed to sense the temperature and relative humidity of the gas-air mixture. When used, the temperature and humidity sensors are coupled to the processor circuit such that the processor circuit can determine the LEL according to the sensed temperature and the sensed relative humidity.

In one aspect, the method, system, and apparatus provide improved accuracy, to about five percent error, in determining LEL levels of certain gases in hot and humid conditions, such as greater than about 37 degrees Celsius (about 99 degrees Fahrenheit) and greater than about 80% relative humidity. By adjusting the LEL according to the measured humidity and temperature of the air, error introduced by such conditions is substantially reduced. Accordingly, safety is improved, and downtime caused by false positive readings of dangerous conditions is reduced. In yet another aspect, the method, system, and apparatus automatically determines the LEL levels corrected for environmental temperature and humidity can be optionally corrected through incorporation of a pressure detector to further improve the accuracy of the system. Such pressure measurements can be especially useful in a mobile platform that may traverse mountainous terrain.

Humidity can also have an optical effect on the light detectors that can require correction at the stage of determining the amount of target gas in the measurement volume. In one approach, the system includes one or more active optical channel(s) designed to primarily detect light absorbed by the target gases and a reference channel that primarily detects light significantly less absorbed by the presence of target gas. Water vapor can attenuate light detected by the reference and active channels in different proportions affecting the determined amount of target gas. Accordingly, the processor can be configured to correct the determined amount of target gas in the volume of gas-air mixture based on the humidity of the volume of gas-air mixture. By one approach, the processor can be configured to correct the determined amount of target gas in the volume of gas-air mixture at least in part by calculating a correction factor from attenuation values determined according to an empirical function, for example polynomial functions, describing attenuation of light by the humidity for at least one light detector and at least one reference channel.

BRIEF DESCRIPTION OF THE DRAWINGS

The above needs are at least partially met through provision of the improved gas detector system and method described in the following detailed description, particularly when studied in conjunction with the drawings, wherein:

FIG. 1 comprises a block diagram of a gas detection system as configured in accordance with various embodiments of the invention;

FIG. 2 comprises a view of an embodiment of a light source and light detector with a gas chamber as configured in accordance with various embodiments of the invention;

Figure 3:
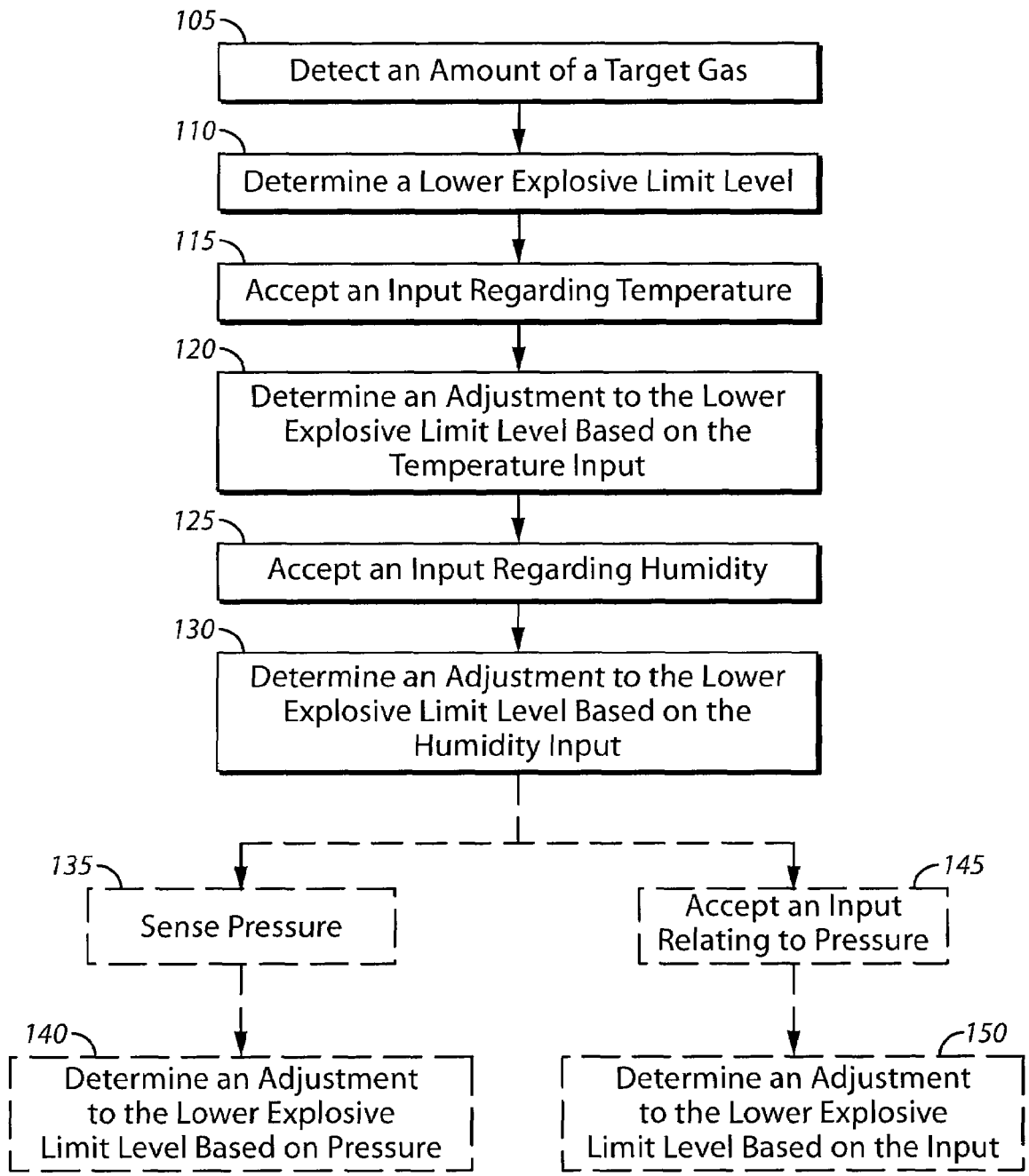
FIG. 3 comprises a flow diagram depicting a method of use as configured in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Referring now to the drawings, and in particular to FIG. 1, a system for sensing gases includes a gas detector 10 including at least one light emitter 12 and at least one light detector 20. The light from the light emitter 12 passes through a volume 30 of gas-air mixture such that a target gas naturally absorbs certain wavelengths out of the light spectrum passing through the volume 30. The light detector 20 is configured to detect an intensity of light at one or more wavelengths spanning portions of a target gas absorption spectrum to detect attenuation of the light at those wavelengths. In other words, if the light that shines through the volume of gas-air mixture is absorbed at certain wavelengths that a certain gas will absorb, then that gas is likely present, and the amount of light absorbed at those wavelengths generally corresponds to the amount of that gas in the gas-air mixture.

By one approach, the gas detector 10 comprises a plurality of light detectors configured to detect different wavelengths of light such that the gas detector 10 may detect a plurality of target gases. For example, the light detector 20 as shown in FIG. 1 may comprise an array of light detectors, wherein each detector may include a light or optical filter 22 configured to attenuate the light from the light emitter 12 to a specific wavelength meaningful for detecting and measuring specific target gases. In a typical embodiment for detecting multiple target gases, each filter 22 corresponds to a different detector 24 and amplifier 26, which amplifies the signal from each detector 24. An analog to digital converter 28 receives the amplified signals and converts the signals to digital signals to be received by a processor circuit 40. By another approach, a single light detector 20 with a single filter, detector, and amplifier may be used for a particular application. Other configurations of the light detector 20 are possible and within the scope of this disclosure. For example, a detector-filter combination that is not affected by the target gas(es) is typically included as a reference channel to compensate for light source aging, deterioration of light transmission due to contamination, and the like.

The processor circuit 40 and a data storage device 42 are coupled to the gas detector 10 and configured to determine an amount of target gas in the volume of gas-air mixture and an LEL level for at least one target gas in the volume. The processor circuit 40 receives the data from the light detector 20 and compares the data against signature absorption levels stored in the data storage device 42 for the target gases the system may be configured to detect. The signature absorption levels are determined during the design and fabrication stage of the system where tests are performed for each target gas for a given system, such that the target gas concentration (or number of molecules of target gas in the measured volume of gas-air mixture) is known for a given light attenuation level. In other words, the processor circuit 40 compares the attenuation levels from the light detector 20 to attenuation levels, which are determined during system fabrication and stored in the data storage device 42, to determine the amount of target gas in the volume that corresponds to the measured light attenuation level. The signature absorption level tables are typically developed during manufacture of the system assuming standard temperature (293.15 Kelvin ("K") (20 degrees Celsius or 68 degrees Fahrenheit)), standard pressure (760 millimeters mercury ("mm Hg") (about 14.7 pounds per square inch), and dry air. Accordingly, the LEL levels produced by the processor circuit 40 and data storage device 42 are subject to those assumptions. Additional details regarding the gas detector 10 can be found in U.S. Patent No. 6,545,278, which is co-owned with this application and which disclosure is incorporated entirely within by reference as if fully rewritten herein.

The amount of oxygen in a gas-air mixture is generally known for standard atmospheric conditions with dry air or zero humidity. Because this amount is known, the amount of target gas in the volume as determined above can be expressed as an LEL level at standard conditions without corrections. For many applications, the LEL level at standard conditions is sufficiently accurate because the amount of oxygen in the air is sufficiently constant. This assumption, however, is not true in areas of temperature and humidity extremes. Adjustments to the LEL level can be computed to convert what essentially is a measurement of the absolute gas concentration of a target gas at standard atmospheric conditions (where the optical absorption has been acquired as instrument calibration) to actual conditions by estimating the about of oxygen.

The gas equation:

$$N*R=20.9\%*P*V/T \qquad \text{Eq. 1}$$

describes the relationship among the pressure P, volume V, and temperature T of a gas with respect to the amount N of the gas in the volume and a constant R. The 20.9% figure represents the amount of oxygen in the atmosphere at standard pressure, standard temperature, and dry air. To compare the effect of a change in an amount of oxygen from standard air assuming a constant volume V, which is true when using a constant size measurement chamber 60, an example of which is shown in FIG. 2, Equation 1 can be re-written to reflect both standard and actual conditions:

$$N_0*R/V=20.9\%*P_0/T_0 \qquad \text{Eq. 2}$$

for standard conditions, $P_0$ and $T_0$, and $$N_1*R/V=20.9\%*P_1/T_1 \qquad \text{Eq. 3}$$

for actual conditions, $P_1$ and $T_1$. Accordingly, the ratio $\epsilon$ of oxygen concentration present in a volume V at actual conditions as compared to standard conditions is the ratio of Equations 2 and 3:

$$\epsilon = N_1/N_0 = (P_1/T_1)/(P_0/T_0) = (T_0 * P_1)/(T_1 * P_0) \quad \text{Eq. 4}$$

where the constants R, V, and 20.9% drop out. Because the LEL level is a derivative of the ratio of target gas to oxygen, or $N_{target\ gas}/N_{oxygen}$, the LEL as determined by the system is the LEL as determined at standard conditions divided by the oxygen correction ratio $\epsilon$:

$$LEL_{corr} = \frac{LEL_{std}}{\epsilon} = LEL_{std} * \frac{T_1 * P_0}{T_0 * P_1} \quad \text{Eq. 5}$$

Also, because the adjustments in LEL level for temperature and pressure (and humidity) are multiplicative in nature, each correction can be done and applied separately and in any order, and each will be described separately below.

With reference again to FIG. 1, to assist in determining an accurate LEL level with adjustments to account for variations in the environment of gas measurement from standard conditions, the system 5 includes an input device 44 coupled to the processor circuit 40. The processor circuit 40 is configured to accept data through the input device 44 relating to or representative of the temperature of the volume 30 of gas-air mixture and to adjust the LEL level according to a function of at least the data representative of temperature. The input device 44 may include an interface for a user, such as a keyboard or other computer-user interface, through which a user may enter data. In general, the temperature input or data can be converted to or is an actual temperature for the measured volume of gas-air mixture. The input or data relating to temperature may be a temperature reading obtained by the user, a temperature range that the user chooses from a list of ranges, or the like. By another approach, the input relating to temperature may be obtained over a network connection such as a local network or the Internet, from which information relating to temperature may be downloaded. Optionally, a temperature sensor 50 may be disposed to sense temperature of the volume of gas-air mixture. For example, the temperature sensor 50 is typically disposed inside the measurement volume to obtain an accurate reading. In certain approaches, the light(s) used to provide light for the light detectors can warm the sample volume of gas by about eight Celsius (14 Fahrenheit). If an external temperature is used, a correction for such a heating effect can be implemented by those skilled in the art. In such an embodiment, the temperature sensor 50 is in communication with the processor circuit 40 to provide the data relating to the temperature of the volume 30 of gas-air mixture.

The processor circuit 40 is configured to adjust the LEL level according to a function of at least the input or data representative of temperature of the volume 30 of gas-air mixture. The change in LEL based on temperature reflects the change in amount of oxygen in the measured volume of gas-air mixture relative to the assumed amount of oxygen in the volume at standard temperature. For example, hot air is less dense than cooler air; therefore, there is less oxygen in a given volume of hot air in comparison to the same volume of cool air at equal pressure. If there is less oxygen in the gas-air mixture, then fewer molecules of target gas are needed to reach a critical ratio with oxygen, and the LEL should be raised accordingly for a given measured amount of target gas molecules in the volume. Thus, to correct for temperature variations from standard temperature, the LEL level is multiplied by a ratio of the temperature of the volume 30 of gas-air mixture over standard temperature. In other words, the LEL level is multiplied by the factor $T_1$ over $T_0$. This correction is consistent with the correction factor reflected in Equation 5.

Similarly, the processor circuit 40 can be configured to receive an input or data representative of or relating to the humidity of the volume 30 of gas-air mixture and to adjust the LEL level according to a function of at least the input relating to humidity. In general, the humidity input is one that can be converted to or is an actual relative humidity reading for the measured volume of gas-air mixture. The term "humidity" refers to the amount of gaseous or suspended water in a measurement volume. For example, the data relating to humidity may be a relative humidity reading obtained and entered by the user through the input device 44, a humidity range that the user chooses from a list of ranges, or the like. By another approach, the input relating to humidity may be obtained over a network connection such as a local network or the Internet, from which information relating to humidity may be downloaded. Optionally, a relative humidity sensor 52 may be disposed to sense relative humidity of the volume 30 of gas-air mixture. By one approach, a combination temperature and humidity sensor may be used, such as a SENSIRION SHT11 sensor sold by SENSIRION AG of Switzerland. In such an embodiment, the relative humidity sensor 52 is in communication with the processor circuit 40 to provide the data representative of the relative humidity of the volume 30 of gas-air mixture. Although this disclosure uses the expression "relative humidity" with respect to the operation of the device described herein, it should be understood that a measurement of absolute humidity would be just as useful for the purposes described herein.

The processor circuit 40 is configured to adjust the LEL level according to a function of at least the input relating to relative humidity of the volume 30 of gas-air mixture. Humidity, or water vapor in the air, acts to displace oxygen relative to the amount of oxygen that is assumed to be present in dry air. As described above with respect to temperature, if there is less oxygen in the gas-air mixture, then fewer molecules of target gas are needed to reach a critical ratio with oxygen, and the LEL should be raised accordingly. The amount of water vapor in air, and thus, the amount of oxygen displaced in the air, can be described in terms of its partial pressure, $P_{H2O}$, which as known in the art is calculated by multiplying the relative humidity, Rh, and the saturation pressure of water vapor, $Psat_{H2O}(t)$:

$$P_{H2O} = Rh * Psat_{H2O}(t) \quad \text{Eq. 6}$$

at a given temperature, t. The saturation pressure, $Psat_{H2O}(t)$, varies with temperature, and this variation can be estimated for temperatures above zero Celsius (thirty two Fahrenheit) using the following known equation:

$$Psat_{H2O}(t) = 6.5805*10^{-6}*t^4 - 1.1226*10^{-4}*t^3 + 0.017615*t^2 + 0.33381*t + 4.0001 \quad \text{Eq. 7}$$

The water vapor partial pressure as thus determined, can be used to adjust the LEL level by multiplying the LEL level by a factor comprising $760/(760 - P_{H2O})$, in other words, the ratio of the standard pressure (760 mmHg) to the standard pressure minus the water vapor partial pressure. The factor represents a ratio of the amount of air taken up the water vapor, which ratio equally applies to describe the amount of oxygen displaced. Accordingly, if the relative humidity is high, the amount of displaced oxygen is high, and the correction factor increases the LEL level.

Humidity can also have an optical effect on the light detectors that can require correction at the stage of determining the amount of target gas in the measurement volume. In one approach, the system 5 includes one or more active optical channel(s) that are designed to primarily detect light absorbed by the target gases and a reference channel that primarily detects light significantly less absorbed by the presence of target gas. Water vapor can attenuate light detected by the reference and active channels in different proportions affecting the determined amount of target gas. Accordingly, the processor circuit 40 and data storage device 42 are configured to correct the determined amount of target gas in the volume of gas-air mixture based on the data representative of humidity of the volume of gas-air mixture. By one approach, the processor circuit 40 can be configured to correct the determined amount of target gas in the volume of gas-air mixture at least in part by calculating a correction factor from attenuation values determined according to an empirical function, such as polynomial functions describing attenuation of light by the humidity for at least one light detector and at least one reference channel. The attenuations caused by humidity are approximated by polynomial functions. In the following example, the two wavelengths used for the sensors are 3.95 μm for the reference channel and 3.43 μm for the active channel.

Denoting absolute humidity as AH, measured as partial pressure of the water content in air divided by the standard air pressure, the polynomials that describe the attenuation caused by atmospheric humidity become:

$$Ra = -0.277474*AH + 1.0 \qquad \text{Eq. 8}$$

$$Aa = -0.876244*AH^2 - 0.362138*AH + 1.0 \qquad \text{Eq. 9}$$

where Ra is the reference channel attenuation and Aa is the active channel attenuation. The exact form of the polynomial depends on the specific optical filters used for the active and reference channels. For example, in one approach, the attenuation for each of the optical channels is measured in experiments where the humidity content and temperature are well controlled and measured. An example set of conditions might be:
Temp=20C: Relative Humidity=0, 20%, 40%, 60%, 80%;
Temp=40C: Relative Humidity=0, 20%, 40%, 60%, 80%;
Temp=60C: Relative Humidity=0, 20%, 40%, 60%, 80%;
Temp=80C: Relative Humidity=0, 20%, 40%, 60%, 80%.
Once all these conditions have been recorded, the results of attenuation are plotted versus humidity (with temperature as parameter), for example in a spreadsheet program such as MICROSOFT EXCEL. Then, a polynomial function can be fit to the plot through the experimental points and to determine which order (linear, quadratic, cubic, and the like) best matches the experimental points. Accordingly, the polynomial function fit the data can be used as the function for a particular channel.

To apply this correction to the determination of target gas amount in the volume, a ratio of the active channel amplitude A to the reference amplitude R is determined as follows to obtain the optical absorption OA caused by the target gas:

$$OA = (A/Ao)/(R/Ro) \qquad \text{Eq. 10}$$

where Ao and Ro are respectively the active and reference channel amplitudes during "Zero gas" calibration, in other words, calibration with dry standard air flowing through the gas detector.

To account for the light absorption by the humidity, the values of Ao and Ro must be multiplied by the corresponding attenuations such that the formula for OA becomes:

$$OA = (A/(Ao*Aa))/(R/(Ro*Ra)) \qquad \text{Eq. 11}$$

This correction factor is then applied to the determination of the amount of target gas in the measurement volume by multiplying the correction factor by the measured attenuation level for a given wavelength of light prior to the additional corrections for pressure, temperature, and humidity described above.

After applying the above corrections to the LEL calculation, the system 5 may then display the LEL level for the one or more target gases on a display 46, such as a screen. The display 46 may include lights, sirens, or other warning displays and/or transmit electronic signals to central monitoring equipment as may be necessary to quickly notify workers of a potentially dangerous working situation.

FIG. 2 shows an embodiment of the system 5 using a chamber 60 in which the volume 30 of gas-air mixture can be placed such that the light emitter 12 and light detector 20 can sense the attenuation of light by the target gas(es). The gas-air mixture is caused to enter the chamber 60 through an inlet 62 and exit through an outlet 64. The manner in which the gas-air mixture is drawn into the chamber 60 is such that the conditions of the gas-air mixture inside the chamber, such as pressure, temperature, and humidity, substantially match the conditions of the outside air, for example by creating convection flow or having some other fluid connection between the inside of the chamber 60 and the outside atmosphere. A temperature sensor 50 and humidity sensor 52 may be disposed within the chamber 60 so as to not interfere with the even distribution of light toward the light detector 20. By another approach, the temperature sensor 50 and humidity sensor 52 may be disposed outside of the chamber 60 to measure the conditions of the gas-air mixture being introduced to the chamber 60. For example, the various sensors may be disposed at a central weather station that communicates humidity, temperature, and pressure measurements to a number of relatively closely positioned sensor systems 5.

With reference again to FIG. 1, optionally, a pressure sensor 54 may be disposed to sense pressure of the volume 30 of gas-air mixture and in communication with the processor circuit 40 such that the processor circuit 30 can adjust the LEL level according to a sensed pressure of the volume 30. Like the temperature sensor 50 and relative humidity sensor 52, the pressure sensor 54 may be disposed within or outside of the chamber 60 to detect the pressure of the air measured by the system. Although the LEL level often need not be adjusted for normal atmospheric variations in pressure, applications deep underground, for example, in a mine shaft, or high above sea level on a mountain do experience some error due to variation from standard pressure. For example, the air at 2000 m above sea level has a density 20% lower than air at sea level, and air at 2000 m below sea level is 26% denser than air at sea level. The dense air far below sea level results in a higher amount of oxygen in the gas-air mixture when compared to standard pressure, necessitating a larger amount of target gas to reach a critical ratio with the oxygen. The reverse is true at high altitude. Accordingly, the LEL level is adjusted by multiplying the LEL level by a ratio of the standard pressure over sensed pressure, $P_0$ to $P_1$, thereby lowering the LEL at higher pressures and raising the LEL level at lower pressures. This correction is consistent with the correction factor reflected in Equation 5, above.

By a different approach, the correction for pressure may be accomplished through a separate input or data from a user through the input device 44. Because variations in pressure due to atmospheric conditions have a near negligible effect on the LEL calculation relative to pressure variations due to large altitude changes, the correction for pressure can be done without actual measurement of the ambient air pressure. In one such approach, the processor circuit 40 is configured to accept an input or data relating to a pressure of the volume of gas-air mixture and to adjust the LEL level according to a function of the pressure of the volume of gas-air mixture as described herein. The input may be, for example, an input relating to altitude of the system or the pressure of the air. The data storage device 42 may then store tables cross-referencing a typical air pressure for various altitudes as may be entered by a user. These pressures can then be used to correct the LEL level as described herein. By another approach, the input may be a pressure reading taken and entered by a user of the system. Another example input includes a pressure range that the user chooses from a list of ranges. The input relating to pressure may also be obtained over a network connection such as a local network or the Internet, from which information relating to altitude or pressure may be downloaded. By another approach, a GPS (global positioning device) may be used to obtain the altitude.

By another approach, an apparatus for determining an LEL level with adjustments based on sensed temperature and sensed humidity includes a gas detector 10 comprising at least one light emitter 12 and at least one light detector 20 configured to detect an intensity of light at wavelengths corresponding to a target gas absorption spectrum in a volume 30 of gas-air mixture, a humidity sensor 52 disposed to sense humidity relating to the gas-air mixture, and a temperature sensor 50 disposed to sense temperature relating to the gas-air mixture. A processor circuit 40 is in communication with the gas detector 10, the humidity sensor 52, and the temperature sensor 50 wherein the processor circuit 40 is configured to determine an amount of at least one target gas in the volume 30 of gas-air mixture and to determine an LEL level for at least one target gas in the volume of gas-air mixture based on the amount of target gas in the volume of gas-air mixture and on signals from the humidity sensor and the temperature sensor.

By yet another approach, an apparatus for determining an adjusted LEL level includes a gas detector 10, temperature sensor 50, humidity sensor 52, and a pressure sensor 54 disposed to sense pressure relating to the gas-air mixture. In this approach, the pressure sensor 54 is in communication with the processor circuit 40 wherein the processor circuit 40 is configured to determine the LEL level for at least one target gas in the volume of gas-air mixture based on data from the pressure sensor 54 in addition to data from the temperature sensor 50 and humidity sensor 52. By taking into account corrections for each of the above atmospheric factors, an apparatus or system for detecting LEL level for one or more gases can achieve determination of the LEL level with an error rate of at most approximately five percent in a variety of atmospheric conditions, such as in hot and humid conditions where error levels may increase for certain prior LEL level detector systems.

Those skilled in the art will recognize and understand that a system or apparatus such as depicted in FIGS. 1 and 2 may comprise a plurality of physically distinct elements as is suggested by the illustrations. It is also possible, however, to view the illustrations as comprising a logical view, in which case one or more of these elements can be enabled and realized via a shared platform. For example, the various air sensors may be combined into a single sensor unit. Similarly, the processor circuit and data storage device may be disposed in separate or combined platforms. For example, the data storage device may include a memory circuit integral with or separate from the processor circuit. It will also be understood that such shared or separate platforms may comprise wholly or at least partially programmable platforms as are known in the art.

FIG. 3 illustrates an example process 100 as may be performed to provide an LEL level for one or more target gases in a gas-air mixture. The system at step 105 detects an amount of a target gas in the volume 30 of gas-air mixture. This step will typically include determining the number of molecules of target gas in the volume 30 or a concentration relative to an expected gas-air mixture using, for example, the gas detector 10 and processor circuit 40. At step 110, the system determines an LEL level for the target gas. This step 110 is typically done by converting the concentration of target gas determined in step 105 to an LEL level based on tests performed on the system during fabrication based. The conversion is typically based on assumptions of standard temperature, standard pressure, and dry air because these assumptions are true for many applications.

At step 115, an input is accepted regarding a temperature for the volume 30 of gas-air mixture. As described above, a temperature sensor 50 may sense a temperature for the volume 30 of gas-air mixture to provide the input or data regarding temperature. The sensor 50 may detect the temperature directly by placing the sensor 50 in the gas-air mixture, by sensing the temperature of the chamber 60, or by sensing the temperature of the atmosphere from which the gas-air mixture to be tested is drawn. Other approaches include a user's providing the input regarding temperature or obtaining the input via a network, for example. The system at step 120 determines an adjustment to the LEL level determined in step 110 based on the input regarding temperature of the volume 30 of gas-air mixture. This step 120 is typically performed by multiplying the LEL level by a ratio of the temperature of the gas-air mixture over standard temperature as described above.

An input is accepted regarding humidity for the volume 30 of gas-air mixture at step 125. A relative humidity sensor 52 may sense a relative humidity of the volume 30 and provide the input as described above. Like the temperature sensor 50, the relative humidity sensor 52 may be in direct contact with the tested volume 30 of gas-air mixture in a testing chamber 60, or the sensor 52 may sense the relative humidity of the atmosphere from which the tested gas-air mixture is drawn. The input may be accepted from a network or other methods as described herein. The system then determines an adjustment to the LEL level based on the input regarding a relative humidity of the volume 30 of gas-air mixture at step 130. The system performs the adjustment by calculating a partial pressure of water vapor in the volume 30 of gas-air mixture using a temperature and a relative humidity of the gas-air mixture, each of which may be derived from their corresponding inputs, and multiplying the LEL level by a factor comprising ambient pressure/(ambient pressure—the partial pressure of water vapor), where ambient pressure is the pressure of the gas-air mixture, which is generally 760 mmHg at sea level. If the method is performed at other than standard pressure conditions, the ambient pressure may be determined by sensing the pressure of the volume of gas-air mixture at step 135 or by accepting an input relating to pressure at step 145 as described below. The partial pressure of water vapor in the volume 30 of gas-air mixture is calculated using the sensed temperature and sensed relative humidity by multiplying the relative humidity of the gas-air mixture and an approximation of a saturation pressure of water vapor as described above.

Optionally, the method 100 may also include sensing the atmospheric pressure of the volume of gas-air mixture at step 135 and determining an adjustment to the LEL level based on the sensed pressure at step 140. Like the temperature sensor 50, the pressure sensor 54 may be in direct contact with the tested volume 30 of gas-air mixture in a testing chamber 60, or the sensor 54 may sense the pressure of the atmosphere from which the tested gas-air mixture is drawn. The adjustment to the LEL level includes multiplying the LEL level by a ratio of the standard pressure over sensed pressure.

Another approach to correcting for pressure is noted at step 145 wherein the system may accept an input relating to a pressure of the volume 30 of gas-air mixture. At step 150 the LEL level is adjusted according to the input. The input may simply be an input of pressure by a user of the system or a figure other loaded into the system as described above. Because atmospheric variations in pressure typically to do not introduce significant error relative to pressure differences experienced at extreme altitudes, the input may relate to an altitude of the system. The altitude may be input, and the system may determine the correction to the LEL based on a known and stored correlation of approximate atmospheric pressure to altitude according to the teachings of this disclosure.

Those skilled in the art will appreciate that the above-described processes are readily enabled using any of a wide variety of available and/or readily configured platforms, such as the processor circuit 40 and data storage device 42 disclosed herein, including partially or wholly programmable platforms as are known in the art or dedicated purpose platforms as may be desired for some applications. Those skilled in the art will recognize and appreciate that such architecture can comprise a fixed-purpose hard-wired platform or can comprise a partially or wholly programmable platform. All of these architectural options are well known and understood in the art and require no further description here.

The system and processes described herein, therefore, allow for increased accuracy in the determination of an LEL level for gases over a wider range of atmospheric conditions. In embodiments incorporating the various condition sensors disclosed herein, the device automatically makes these corrections. In extreme conditions, such as in hot, humid air, the improved accuracy improves the safety of workers and limits false positive readings that cause unnecessary down time.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

What is claimed is:

1. A system for sensing gases, the system comprising:
   a gas detector comprising at least one light emitter and at least one light detector configured to detect light at wavelengths spanning a target gas absorption spectrum in a volume of gas-air mixture;
   a processor circuit and a data storage device in communication with the gas detector, the processor circuit and data storage device effective for determining an amount of target gas in the volume of gas-air mixture and a lower explosive limit level for at least one target gas in the volume of gas-air mixture;
   wherein the processor circuit is configured to receive data representative of temperature of the volume of gas-air mixture and adjusts the lower explosive limit level according to a function of at least the data representative of temperature of the volume of gas-air mixture;
   wherein the processor circuit is configured to receive data representative of humidity of the volume of gas-air mixture and adjusts the lower explosive limit level according to a function of at least the data representative of humidity of the volume of gas-air mixture;
   wherein the function of at least the data representative of humidity of the volume further comprises calculating a partial pressure of water vapor in the volume of gas-air mixture using the input relating to temperature of the volume of gas-air mixture and a humidity of the volume of gas-air mixture and multiplying the lower explosive limit level by a factor comprising ambient pressure divided by (ambient pressure—the partial pressure of water vapor).

2. The system of claim 1 wherein the gas detector comprises a plurality of light detectors configured to detect different wavelengths of light such that the gas detector may detect a plurality of target gases.

3. The system of claim 1 wherein the processor circuit and data storage device are configured to determine the lower explosive limit level for at least one target gas in the volume of gas-air mixture assuming standard temperature, standard pressure, and dry air.

4. The system of claim 1 wherein the function of at least the data representative of temperature of the volume further comprises multiplying the lower explosive limit level by a ratio of a temperature of the volume of gas-air mixture over standard room temperature.

5. The system of claim 1 wherein the function of at least the data representative of temperature of the volume further comprises calculating a partial pressure of water vapor in the volume of gas-air mixture using the input relating to temperature of the volume of gas-air mixture.

6. The system of claim 1 further comprising a temperature sensor disposed to sense temperature of the volume of gas-air mixture and in communication with the processor circuit to provide the data representative of the temperature of the volume of gas-air mixture.

7. The system of claim 1 further comprising a humidity sensor disposed to sense humidity of the volume of gas-air mixture and in communication with the processor circuit to provide the data representative of the humidity of the volume of gas-air mixture.

8. A system for sensing gases, the system comprising:
   a gas detector comprising at least one light emitter and at least one light detector configured to detect light at wavelengths spanning a target gas absorption spectrum in a volume of gas-air mixture;
   a processor circuit and a data storage device in communication with the gas detector, the processor circuit and data storage device effective for determining an amount of target gas in the volume of gas-air mixture and a lower explosive limit level for at least one target gas in the volume of gas-air mixture;
   a pressure sensor disposed to sense pressure of the volume of gas-air mixture and in communication with the processor circuit wherein the processor circuit adjusts the lower explosive limit level according to a sensed pressure of the volume of gas-air mixture;
   wherein the processor circuit is configured to receive data representative of temperature of the volume of gas-air mixture and adjusts the lower explosive limit level according to a function of at least the data representative of temperature of the volume of gas-air mixture;
   wherein the processor circuit is configured to receive data representative of humidity of the volume of gas-air mixture and adjust the lower explosive limit level according to a function of at least the data representative of humidity of the volume of gas-air mixture;

wherein the processor circuit is configured to adjust the lower explosive limit level according to the sensed pressure of the volume of gas-air mixture by multiplying the lower explosive limit level by a ratio of the standard pressure over sensed pressure.

9. The system of claim 1 wherein the processor circuit receives data representative of pressure of the volume of gas-air mixture and adjusts the lower explosive limit level according to a function of the data representative of pressure of the volume of gas-air mixture.

10. The system of claim 9 wherein the data representative of pressure comprises data relating to altitude.

11. A system for sensing gases, the system comprising:
a gas detector comprising at least one light emitter and at least one light detector configured to detect light at wavelengths spanning a target gas absorption spectrum in a volume of gas-air mixture;
a processor circuit and a data storage device in communication with the gas detector, the processor circuit and data storage device effective for determining an amount of target gas in the volume of gas-air mixture and a lower explosive limit level for at least one target gas in the volume of gas-air mixture;
wherein the processor circuit is configured to receive data representative of temperature of the volume of gas-air mixture and adjusts the lower explosive limit level according to a function of at least the data representative of temperature of the volume of gas-air mixture;
wherein the processor circuit is configured to receive data representative of humidity of the volume of gas-air mixture and adjusts the lower explosive limit level according to a function of at least the data representative of humidity of the volume of gas-air mixture;
wherein the processor circuit and data storage device are configured to correct the determined amount of target gas in the volume of gas-air mixture based on the data representative of humidity of the volume of gas-air mixture;
wherein the processor circuit is configured to correct the determined amount of target gas in the volume of gas-air mixture at least in part by calculating a correction factor from attenuation values determined according to polynomial functions describing attenuation of light by the humidity for at least one light detector and at least one reference channel.

12. A method of determining a lower explosive limit level for at least one gas in a volume of gas-air mixture, the method comprising:
detecting an amount of a target gas in the volume of gas-air mixture;
determining a lower explosive limit level for said target gas;
accepting an input regarding a temperature for the volume of gas-air mixture;
determining an adjustment to the lower explosive limit level based on the input regarding a temperature of the volume of gas-air mixture;
accepting an input regarding a humidity of the volume of gas-air mixture;
determining an adjustment to the lower explosive limit level based on the input regarding a humidity and temperature of the volume of gas-air mixture;
wherein the determining an adjustment to the lower explosive limit level based on the input regarding the relative humidity of the volume of gas-air mixture further comprises calculating a partial pressure of water vapor in the volume of gas-air mixture using a temperature of the volume of gas-air mixture and a humidity of the volume of gas-air mixture and multiplying the lower explosive limit level by a factor comprising ambient pressure divided by (ambient pressure—the partial pressure of water vapor).

13. The method of claim 12 wherein the step of determining an adjustment to the lower explosive limit level based on the input regarding temperature of the volume of gas-air mixture further comprises multiplying the lower explosive limit level by a ratio of a temperature of the volume of gas-air mixture over standard room temperature.

14. The method of claim 12 wherein calculating the partial pressure of water vapor in the volume of gas-air mixture using the temperature and the humidity comprises multiplying the humidity and an approximation of a saturation pressure of water vapor.

15. A method of determining a lower explosive limit level for at least one gas in a volume of gas-air mixture, the method comprising:
detecting an amount of a target gas in the volume of gas-air mixture;
determining a lower explosive limit level for said target gas;
accepting an input regarding a temperature for the volume of gas-air mixture;
determining an adjustment to the lower explosive limit level based on the input regarding a temperature of the volume of gas-air mixture;
accepting an input regarding a humidity of the volume of gas-air mixture;
determining an adjustment to the lower explosive limit level based on the input regarding a humidity and temperature of the volume of gas-air mixture;
sensing a pressure of the volume of gas-air mixture and determining an adjustment to the lower explosive limit level based on the pressure of the volume of gas-air mixture;
wherein the determining an adjustment to the lower explosive limit level based on the pressure of the volume of gas-air mixture further comprises multiplying the lower explosive limit level by a ratio of standard atmosphere pressure over sensed pressure.

16. The method of claim 12 further comprising accepting an input relating to a pressure of the volume of gas-air mixture and adjusting the lower explosive limit level according to the input.

17. The method of claim 16 wherein the input comprises an input relating to altitude.

18. The method of claim 12 wherein the step of accepting an input regarding a temperature for the volume of gas-air mixture further comprises sensing a temperature for the volume of gas-air mixture.

19. The method of claim 12 wherein the step of accepting an input regarding a humidity for the volume of gas-air mixture further comprises sensing a humidity for the volume of gas-air mixture.

20. A method of determining a lower explosive limit level for at least one gas in a volume of gas-air mixture, the method comprising:
detecting an amount of a target gas in the volume of gas-air mixture;
determining a lower explosive limit level for said target gas;
accepting an input regarding a temperature for the volume of gas-air mixture;

determining an adjustment to the lower explosive limit level based on the input regarding a temperature of the volume of gas-air mixture;

accepting an input regarding a humidity of the volume of gas-air mixture;

determining an adjustment to the lower explosive limit level based on the input regarding a humidity and temperature of the volume of gas-air mixture;

correcting the detection of the amount of the target gas in the volume of gas-air mixture based on the input regarding the humidity of the volume of gas-air mixture;

wherein the correcting the detection of the amount of the target gas in the volume of gas-air mixture based on the input regarding the humidity of the volume of gas-air mixture further comprises calculating a correction factor from attenuation values determined according to polynomial functions describing attenuation of light by the humidity for at least one light detector and at least one reference channel.

21. An apparatus for sensing gases, the apparatus comprising:

a gas detector comprising at least one light emitter and at least one light detector configured to detect light at wavelengths corresponding to a target gas absorption spectrum in a volume of gas-air mixture;

a humidity sensor disposed to sense humidity relating to the gas-air mixture;

a temperature sensor disposed to sense temperature relating to the gas-air mixture;

a processor circuit in communication with the gas detector, the humidity sensor, and the temperature sensor, the processor circuit is effective for determining an amount of at least one target gas in the volume of gas-air mixture and to determine a lower explosive limit level for at least one target gas in the volume of gas-air mixture based on the amount of target gas in the volume of gas-air mixture and on data from the humidity sensor and the temperature sensor;

wherein the lower explosive limit level is determined with an error rate of at most approximately five percent in hot and humid conditions.

22. The apparatus of claim 21 further comprising a pressure sensor disposed to sense pressure relating to the gas-air mixture and in communication with the processor circuit wherein the processor circuit is effective for determining the lower explosive limit level for at least one target gas in the volume of gas-air mixture based on data from the pressure sensor.

23. The apparatus of claim 21 wherein the processor circuit is configured to correct the determined amount of target gas in the volume of gas-air mixture based on the humidity of the volume of gas-air mixture.

24. The apparatus of claim 23 wherein the processor circuit corrects the determined amount of target gas in the volume of gas-air mixture at least in part by calculating a correction factor from attenuation values determined according to polynomial functions describing attenuation of light by the humidity for at least one light detector and at least one reference channel.

25. A system for sensing gases, the system comprising:

a gas detector comprising at least one light emitter and at least one light detector configured to detect light at wavelengths spanning a target gas absorption spectrum in a volume of gas-air mixture;

a processor circuit and a data storage device in communication with the gas detector, the processor circuit and data storage device effective for determining an amount of target gas in the volume of gas-air mixture and a lower explosive limit level for at least one target gas in the volume of gas-air mixture;

wherein the processor circuit is configured to receive data representative of temperature of the volume of gas-air mixture and adjusts the lower explosive limit level according to a function of at least the data representative of temperature of the volume of gas-air mixture;

wherein the processor circuit is configured to receive data representative of humidity of the volume of gas-air mixture and adjusts the lower explosive limit level according to a function of at least the data representative of humidity of the volume of gas-air mixture;

wherein the lower explosive limit level is determined with an error rate of at most approximately five percent in hot and humid conditions.

26. A method of determining a lower explosive limit level for at least one gas in a volume of gas-air mixture, the method comprising:

detecting an amount of a target gas in the volume of gas-air mixture;

determining a lower explosive limit level for said target gas;

accepting an input regarding a temperature for the volume of gas-air mixture;

determining an adjustment to the lower explosive limit level based on the input regarding a temperature of the volume of gas-air mixture;

accepting an input regarding a humidity of the volume of gas-air mixture;

determining an adjustment to the lower explosive limit level based on the input regarding a humidity and temperature of the volume of gas-air mixture;

determining the lower explosive limit level with an error rate of at most approximately five percent in hot and humid conditions.

27. An apparatus for sensing gases, the apparatus comprising:

a gas detector comprising at least one light emitter and at least one light detector configured to detect light at wavelengths corresponding to a target gas absorption spectrum in a volume of gas-air mixture;

a humidity sensor disposed to sense humidity relating to the gas-air mixture;

a temperature sensor disposed to sense temperature relating to the gas-air mixture;

a processor circuit in communication with the gas detector, the humidity sensor, and the temperature sensor, the processor circuit is effective for determining an amount of at least one target gas in the volume of gas-air mixture and to determine a lower explosive limit level for at least one target gas in the volume of gas-air mixture based on the amount of target gas in the volume of gas-air mixture and on data from the humidity sensor and the temperature sensor;

wherein the processor circuit is configured to calculate a partial pressure of water vapor in the volume of gas-air mixture using the data from the humidity sensor and the temperature sensor and to multiply the lower explosive limit level by a factor comprising ambient pressure divided by (ambient pressure—the partial pressure of water vapor).

28. An apparatus for sensing gases, the apparatus comprising:

a gas detector comprising at least one light emitter and at least one light detector configured to detect light at wavelengths corresponding to a target gas absorption spectrum in a volume of gas-air mixture;

a humidity sensor disposed to sense humidity relating to the gas-air mixture;

a temperature sensor disposed to sense temperature relating to the gas-air mixture;

a processor circuit in communication with the gas detector, the humidity sensor, and the temperature sensor, the processor circuit is effective for determining an amount of at least one target gas in the volume of gas-air mixture and to determine a lower explosive limit level for at least one target gas in the volume of gas-air mixture based on the amount of target gas in the volume of gas-air mixture and on data from the humidity sensor and the temperature sensor;

a pressure sensor disposed to sense pressure relating to the gas-air mixture and in communication with the processor circuit wherein the processor circuit is effective for determining the lower explosive limit level for at least one target gas in the volume of gas-air mixture based on data from the pressure sensor;

wherein the processor circuit is configured to adjust the lower explosive limit level according to a function of at least the data from the humidity sensor;

wherein the processor circuit is configured to adjust the lower explosive limit level according to the data from the pressure sensor by multiplying the lower explosive limit level by a ratio of the standard pressure over sensed pressure.

29. An apparatus for sensing gases, the apparatus comprising:

a gas detector comprising at least one light emitter and at least one light detector configured to detect light at wavelengths corresponding to a target gas absorption spectrum in a volume of gas-air mixture;

a humidity sensor disposed to sense humidity relating to the gas-air mixture;

a temperature sensor disposed to sense temperature relating to the gas-air mixture;

a processor circuit in communication with the gas detector, the humidity sensor, and the temperature sensor, the processor circuit is effective for determining an amount of at least one target gas in the volume of gas-air mixture and to determine a lower explosive limit level for at least one target gas in the volume of gas-air mixture based on the amount of target gas in the volume of gas-air mixture and on data from the humidity sensor and the temperature sensor;

wherein the processor circuit is configured to correct the determined amount of target gas in the volume of gas-air mixture based on the data from the humidity sensor;

wherein the processor circuit is configured to correct the determined amount of target gas in the volume of gas-air mixture at least in part by calculating a correction factor from attenuation values determined according to polynomial functions describing attenuation of light by the humidity for at least one light detector and at least one reference channel.

* * * * *